United States Patent [19]

Anthony et al.

[11] Patent Number: 4,465,889

[45] Date of Patent: Aug. 14, 1984

[54] CATALYTIC CONVERSION OF METHANOL, DIMETHYL ETHER AND MIXTURES THEREOF TO A HYDROCARBON PRODUCT RICH IN ISO-C$_4$ COMPOUNDS AND NEW CATALYSTS THEREFOR

[75] Inventors: Rayford G. Anthony, Bryan, Tex.; P. E. Thomas, Thottakad, India

[73] Assignee: Summit Gas Systems Pte. Ltd., Jurong, Singapore

[21] Appl. No.: 394,795

[22] Filed: Jul. 2, 1982

[51] Int. Cl.$^3$ .............................................. C07C 1/22
[52] U.S. Cl. ................................... 585/640; 502/71; 502/77; 502/236; 502/239; 502/240; 502/242; 585/408; 585/469; 585/733
[58] Field of Search ............... 585/408, 469, 640, 733, 585/639; 252/455 Z, 449; 502/63, 236, 239, 240, 242

[56] References Cited

U.S. PATENT DOCUMENTS

| | | | |
|---|---|---|---|
| 3,329,480 | 7/1967 | Young | 23/111 |
| 4,013,732 | 3/1966 | Chang et al. | 260/668 R |
| 4,061,724 | 12/1977 | Grose et al. | 585/640 |
| 4,197,418 | 4/1980 | Lee et al. | 585/640 |
| 4,320,241 | 3/1982 | Frankiewicz | 585/640 |

FOREIGN PATENT DOCUMENTS 0035807  9/1981  European Pat. Off. ............ 585/640

OTHER PUBLICATIONS

Anderson et al., J. Catalysis, 58, 114, (1979).
Olson et al., J. Catalysis, 61, 390, (1980).
Wu et al., J. Phys. Chem., 83, 2777, (1979).
Rao et al., ACS, Div. Fuel Chem., (ACFPA), 25(2), 119, (1979).

*Primary Examiner*—Delbert E. Gantz
*Assistant Examiner*—A. Pal
*Attorney, Agent, or Firm*—Robert E. Burns; Emmanuel J. Lobato; Bruce L. Adams

[57] ABSTRACT

Methanol, dimethyl ether or a mixture thereof is converted to a hydrocarbon product rich in iso-C$_4$ compounds by contact with a catalyst comprised of crystalline silica having molecular sieve properties or a crystalline solid with molecular sieve properties which has been impregnated with thorium oxide, zirconium oxide, titanium oxide or a combination thereof.

21 Claims, No Drawings

CATALYTIC CONVERSION OF METHANOL, DIMETHYL ETHER AND MIXTURES THEREOF TO A HYDROCARBON PRODUCT RICH IN ISO-C4 COMPOUNDS AND NEW CATALYSTS THEREFOR

BACKGROUND OF THE INVENTION

This invention relates to a method for converting methanol and/or dimethyl ether to a hydrocarbon product, particularly a hydrocarbon product rich in isobutane and isobutene. The invention is also concerned with new catalysts, by means of which methanol and/or dimethyl ether is converted to a hydrocarbon product rich in iso-C4 compounds.

Isobutene or isobutylene and isobutane are important starting materials for the preparation of a variety of commercially important products, including maleic anhydride-isobutylene copolymer, 2,5-dimethylhexadiene, which is a key intermediate in the manufacturer of pyrethrin insecticides, butyl rubber, polybutenes, methyl methacrylate, alkylate, which is a blending component for high octane gasoline and methyl t-butyl ether, which is also a blending component for high octane gasoline.

At present, isobutylene is obtained generally from the cracking of liquid petroleum or from naturally occurring field butanes. However, the demand for isobutylene far exceeds the supply, and this demand is increasing.

The synthesis of branched chain hydrocarbons from synthesis or water gas, i.e., a mixture of carbon monoxide and hydrogen, has been investigated at the Kaiser Wilhelm Institute For Coal Research, Germany; according to a translation of a report by Pichler and Ziesecke, *Bureau Of Mines Bulletin*, 488, U.S. Government Printing Office, Washington, D.C. 1950, water gas has been converted under high pressure and elevated temperature to a hydrocarbon product containing isobutylene by means of a variety of catalysts, including catalysts composed principally of an oxide of thorium, aluminum, tungsten, chromium, titanium, zirconium, uranium, zinc, manganese or cerium and mixtures of thorium oxide with alumina, zinc oxide, chromium oxide, iron and copper.

While the work of Pichler et al. shows that water gas can be converted into a hydrocarbon product containing iso-C4 hydrocarbons, the Pichler et al. process has serious shortcomings which have prevented its commercial use. In particular, the conversion is carried out at very high pressure, i.e., from 30 to 1,000 atms.; the higher the pressure, the better the conversion; however, high pressure equipment is very expensive. Further, thorium oxide is also costly and the concentration of thorium oxide in the Pichler et al. catalyst is high, i.e., about 71-100 percent by weight.

More recently, crystalline aluminosilicate zeolites or molecular sieves have been disclosed and shown to be useful for catalyzing a variety of reactions. For example, according to U.S. Pat. No. 3,036,134, alcohols may be converted to ethers, by means of a crystalline aluminosilicate of the formula:

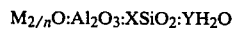

$$M_{2/n}O:Al_2O_3:XSiO_2:YH_2O$$

wherein M is a metal and n its valence, X varies from about 1.35 to 3 and the average value for Y is between 4 and 8.

The dehydration of a normal alcohol to an olefin having a corresponding structure by means of such a synthetic zeolite or molecular sieve is disclosed in U.S. Pat. No. 3,529,033.

According to U.S. Pat. No. 4,079,096, a catalyst of crystalline aluminosilicate zeolite is also useful to convert methanol and/or dimethyl ether to a hydrocarbon product rich in ethylene and propylene. Reactions of polar organic compounds through the use of zeolite catalysts are disclosed in U.S. Pat. No. 3,728,408; the production of aromatic compounds from liquid hydrocarbons using a crystalline aluminosilicate catalyst is taught as U.S. Pat. Nos. 3,756,942 and 3,760,024, and the aromatization of alcohols, ethers and carbonyl-containing compounds by means of a crystalline aluminosilicate zeolite in U.S. Pat. No. 3,894,104. The use of a crystalline aluminosilicate zeolite catalyst to convert lower aliphatic alcohols, carbonyls, ethers and the like to a hydrocarbon product rich in compounds containing 5 or more carbon atoms has been disclosed in U.S. Pat. No. 3,894,103, while the conversion of compound of formula $CH_3X$, wherein X is a hydroxyl, alkoxy, alkylthio, amino, alkylamine dialkylamine, halo or cyano group to aromatic compounds is taught in U.S. Pat. No. 3,894,105, and the conversion of methanol and/or dimethyl ether to a hydrocarbon product rich in ethylene and propylene is taught in U.S. Pat. No. 4,062,905.

German Pat. Nos. 2,827,385 and 2,755,229 also concern the conversion of methanol and/or dimethyl ether by means of a zeolite catalyst to a hydrocarbon product rich in ethylene and propylene.

Recently, a crystalline silica composition of uniform pore diameter, which exhibits molecular sieve and hydrophobic organophilic properties, but not ion exchange properties has been disclosed by Gross et al. in U.S. Pat. No. 4,061,724, which is incorporated herein by reference. According to Gross et al., this silica composition, which is referred to as silicalite is substantially free of alumina except for incidental impurities and the crystals thereof are orthorhombic. Silicalite has also been characterized as a silica polymorph, which after calcination in air at 600° C. for 1 hour, has a mean refractive index of 1.39 and a specific gravity at 25° C. of 1.70. Due to its uniform pore structure, silicalite is disclosed as being useful to separate p-xylene from o-xylene and as being useful for selectively absorbing organic materials from water as a result of its hydrophobic/organophilic properties.

SUMMARY OF THE INVENTION

An object of the present invention is the provision of a process for converting methanol and/or dimethyl ether to hydrocarbons rich in isobutane and isobutene.

Another object of the present invention is the provision of a process for obtaining isobutene and isobutane from methanol and/or dimethyl ether in an economical, commercially feasible process.

A further object of the present invention is the provision of a catalyst, whereby methanol and/or dimethyl ether is converted to a hydrocarbon product rich in iso-C4 compounds.

Another important object of the present invention is a method for producing isobutene in high yield from methanol and/or dimethyl ether.

These and other objects of the invention are achieved by a process of contacting a hydrocarbon feed containing methanol and/or dimethyl ether with a crystalline silica catalyst at elevated temperature.

It has been discovered that methanol and/or dimethyl ether is converted to a hydrocarbon product rich in iso-$C_4$ compounds by contacting methanol and/or dimethyl ether with a catalyst comprised of crystalline silica which has a uniform pore structure and exhibits molecular sieve properties, at a temperature of about 300° to 550° C.

It has further been discovered that a particularly high yield of iso-$C_4$ compounds is obtained by contacting methanol, dimethyl ether or a mixture thereof at a temperature of about 300° to 550° C. with a catalyst having molecular sieve properties which has been impregnated with one or more metal oxides selected from thorium oxide, zirconium oxide and titanium oxide.

DESCRIPTION OF THE INVENTION

The conversion of methanol and/or dimethyl ether to a hydrocarbon product rich in iso-$C_4$ compounds, in accordance with one embodiment of the invention, is carried out by contacting methanol, dimethyl ether or a mixture thereof with a catalyst comprised of crystalline silica which exhibits molecular sieve properties and is substantially free of alumina, such as silicalite disclosed in U.S. Pat. No. 4,061,724. It is critical to use a silica catalyst which is crystalline since amorphous silica is not an effective catalyst for this reaction. Further, a pore size of about 5 to 10 Å, more preferably 5–8 Å, and most preferably 5.2 to 6.5 Å and a uniform pore size are believed to contribute to the effectiveness of the catalyst in this reaction.

In another embodiment of the invention, methanol and/or dimethyl ether is converted to a hydrocarbon product rich in iso-$C_4$ compounds by contact with a catalyst comprised of a crystalline solid exhibiting molecular sieve properties which has been impregnated with an oxide selected from thorium, zirconium, or titanium oxide or a combination thereof. The molecular sieve is comprised of silica and is preferably a crystalline silica or crystalline aluminosilicate of uniform pore diameter. It is also preferable that the catalyst be comprised of crystalline silica having a pore diameter of about 5 to 10 Å, more preferably 5.1 to 8 Å, and most preferably a pore diameter of about 5.2 to 6.5 Å, such as silicalite impregnated with thorium oxide, zirconium oxide and/or titanium oxide. A catalyst which has been impregnated with thorium oxide is particularly preferred.

While catalysts containing up to about 50 parts by weight of oxide may be used, a preferred catalyst of the invention contains from about 0.5 to 30 parts by weight of oxide, and a more preferred catalyst, about 2 to 15 parts by weight of the oxide.

The oxide-containing catalyst may be prepared by any convenient procedure. For example, the crystalline molecular sieve composition may be combined with an aqueous solution of a water soluble salt of the desired metal oxide. After the resultant slurry is dried, the catalytic composition is packed in a reactor and calcined at a temperature which does not destroy the crystal structure of the catalyst, in the range of about 340°–600° C. Thereafter, the catalyst may be cooled and maintained in an inert atmosphere, such as nitrogen, until the temperature is that desired for the reaction.

To produce a hydrocarbon product rich in iso-$C_4$ compounds in accordance with the invention, methanol and/or dimethyl ether, or a mixture thereof, is fed to the reactor into contact with the catalyst. Water may also be fed to the reactor with the methanol and/or dimethyl ether, in an amount up to about 80% by weight of the feed, preferably up to about 70% by weight of the feed.

The temperature of the reactor during the conversion is preferably within the range of about 310°–550° C., more preferably about 330° to 455° C. and most preferably, about 370° to 430° C.

The conversion of methanol and/or dimethyl ether may be carried out at a pressure of about 0.1 to 20 atms., more preferably about 1 to 10 and most preferably 1 to 4 atms. However, while the conversion may be carried out at elevated or reduced pressure, it is a particularly advantageous feature of the process of the invention, that the conversion may be carried out at ordinary atmospheric pressure, so that the expense of high pressure equipment may be avoided.

Methanol, a mixture of methanol and water, dimethyl ether, a mixture of dimethyl ether and methanol, or a mixture of methanol, dimethyl ether and water, can be fed to the reactor; preferred feeds include methanol alone, a mixture of about 90–30% by weight of methanol and 10–70% by weight of water and an equilibrium mixture of methanol, dimethyl ether and water. Equilibrium mixture of methanol, dimethyl ether and water as used herein refers to the mixture which is obtained when these three components establish an equilibrium relative to the reaction:

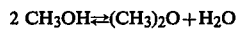

$$2\ CH_3OH \rightleftharpoons (CH_3)_2O + H_2O$$

in the temperature range of 250° to 450° C. Preferably, the mixture is obtained by passing methanol over any dehydration catalyst, known in the art, one of which is γ-alumina, at a temperature of about 250° to 450° C. The equilibrium composition is dependent upon the initial feed composition and the reaction temperature. Therefore, mixtures of: methanol; dimethyl ether and water; methanol and water; or dimethyl ether and water can be converted to an equilibrium mixture at 250° to 450° C. and used as feed to the catalyst described herein. Most economically, crude methanol, containing about 80 to 90% of methanol, with the remainder water, i.e., 10–20% water with minor impurities is used.

The conversion is desirably carried out at a space velocity varying from about 0.1 to 20 WHSV, preferably 0.5 to 10 WHSV and most preferably 0.7 to 5 WHSV.

Ethylene and/or propylene can be recycled to increase the yield of iso-$C_4$ compounds.

In another embodiment of the invention, methanol is converted to a hydrocarbon product rich in iso-$C_4$ compounds in two or three stages. In such a process, a dehydrating catalyst such as γ-alumina is packed near the entrance of the reactor and the iso-$C_4$ producing catalyst, i.e., a silicalite, silicalite-oxide, or other molecular sieve-oxide catalyst, is packed below the alumina. Methanol is then fed to the reactor, which is converted by the γ-alumina in the first stage of the reaction to an equilibrium mixture of dimethyl ether, water and methanol. In the second stage of the reactor, the equilibrium mixture is converted to the hydrocarbon product.

A third stage can be added to the reactor to dehydrogenate isobutane in the hydrocarbon product to the particularly preferred isobutene.

All types of catalytic reactors usual in the art, including a fluidized bed, recycle reactor, moving bed reactor, ebulating bed reactor or a tubular fixed-bed reactor can be used in this process.

Likewise, other methods may be used to incorporate thorium, zirconium or titanium oxide in the catalyst and if desired, an inert carrier or γ-alumina may be present in the catalyst.

By means of the present process, iso-$C_4$ compounds are obtained from methanol, dimethyl ether, a mixture thereof, or a mixture of any of the foregoing with water, in an amount of 10–50% by weight of the gaseous products, and more preferably, in the range of 20 to 50% by weight, and most preferably, in an amount of at least 30% by weight or more.

An advantageous feature of the invention is that the ratio of isobutylene to isobutane in the product may be maintained in the range of about 0.6 to 1.0 by feeding water with methanol or equilibrium mixtures of water, dimethyl ether and methanol to the reactor.

Another feature of this process is that a high content of iso-$C_4$ compounds in the gaseous hydrocarbon product can be maintained with the concomitant production of either a maximum amount of aromatic liquid product or a maximum amount of $C_2$ and $C_3$ hydrocarbons with a high olefinic content. The coproduction of liquid aromatics is reduced by cofeeding water with methanol into contact with the catalyst and by increasing the flow rate.

The following examples, which were carried out at Texas A&M University, College of Engineering, College Station, Tex., further illustrate the best mode currently contemplated for carrying out the invention, but the invention is not limited in any manner thereby.

EXAMPLE 1

Preparation of The Catalyst A

Silicalite S-115 from Union Carbide was calcined at 468° C. for three hours with an air flow rate of 60 cc./min. The calcined catalyst, numbered A-1 in an amount of 90 cc. (44 g.) was placed in a tubular reactor ¾ inch in diameter and approximately 3 feet long in size, surrounded by an electrical heater and fitted with a thermocouple.

Conversion of Methanol to Hydrocarbons

Methanol was fed into the reactor packed with catalyst at a rate of 80 cc./hr. (WHSV—1.45 hr.$^{-1}$) under a pressure of 5.44 atm. The initial reactor temperature of 396° C. rose to 424° C. when methanol was introduced. Methanol conversion was 100%; 23.6 wt. % of the ($CH_2$) group of methanol was converted to organic liquid, i.e., aromatic hydrocarbons. The distribution of gaseous product is set forth in Table 1.

EXAMPLE 2

The catalyst used in Example 1 was regenerated by heating with air at a temperature of 482° C., at an air flow rate of 60 cc./min. After cooling the catalyst to 355° C. with $N_2$, methanol was fed into the reactor (WHSV=1.3 hr.$^{-1}$), whereby the temperature in the reactor rose to 430° C.

The reaction was continued for 85 minutes to yield a total of 54.3 g. of liquid product, including water and 8.24 g. of liquid hydrocarbons. The methanol conversion was 100%; 23.2% of ($CH_2$) was converted to aromatic hydrocarbons which were principally alkylated benzenes. The distribution of gaseous product and parameters of the conversion are set forth in Table 1.

EXAMPLE 3

The catalyst from Example 2 was maintained at 371° C. in a flow of $N_2$ (60 cc./min.) overnight and then cooled to 349° C.

When methanol was fed to the reactor the temperature rose to 432° C.; WHSV=1.63 hr.$^{-1}$.

After 43 minutes, the liquid product collected including

| | |
|---|---|
| $H_2O$ was: | 58.70 g. |
| liquid product excluding $H_2O$: | 15.35 g. |
| $CH_3OH$ conversion: | 100% |
| DME (dimethyl ether) in product: | 0 |
| % ($CH_2$) converted to organic liquid: | 42.9 |

The distribution of the product and parameters of the conversion are shown in Table 1.

EXAMPLE 4

A catalyst used in a preceding example was kept in a current of $N_2$ (60 cc./min.) overnight at 331° C. Methanol was fed into contact with the catalyst in the reactor (WHSV=1.7 hr.$^{-1}$). The following is the temperature profile during the conversion:

| Time (min) | Temp (°C.) |
|---|---|
| 0 | 331 |
| 7 | 371 |
| 13 | 378 |
| 21 | 382 |
| 29 | 379 |
| Conversion of $CH_3OH$ | 100% |
| DME | 0% |

The distribution of the gaseous product and parameters of the conversion are set forth in Table 1.

EXAMPLE 5

A catalyst from a previous example was cooled to 300° C. in a flow of $N_2$ (60 cc./hr.) for 5 hours. Methanol was then fed to the reactor packed with the catalyst; WHSV=1.7 hr.$^{-1}$.

The following is the temperature profile during the conversion.

| Time (min.) | Temp. °C. |
|---|---|
| 0 | 300 |
| 2 | 308 |
| 13 | 317 |
| 20 | 322 |
| 24 | 331 |
| 26 | 337 |
| 27 | 339 |
| 28 | 341 |
| 29 | 343 |
| 30 | 345 |
| 33 | 349 |
| 38 | 353 |
| 42 | 358 |
| 48 | 361 |
| 56–75 | 364 |
| Total weight of liquid product | 2.8 g. |
| % ($CH_2$) conversion to organic liquid | 7 |

The parameters of the conversion and distribution of gaseous product are set forth in Table 1.

TABLE 1

| Ex. No. | Cat. | CONVERSION CONDITIONS | | | Sample Time (min.) | PRODUCT DISTRIBUTION - WT. % | | | | | | |
|---|---|---|---|---|---|---|---|---|---|---|---|---|
| | | Pressure (atm.) | TEMP. °C. | FLOW RATE CC./hr. | | $i$-$C_4H_{10}$ | $n$-$C_4H_{10}$ | 1-$C_4H_8$ | $i$-$C_4H_8$ | trans 2-$C_4H_8$ | cis 2-$C_4H_8$ | $C_3H_8$ |
| 1 | A-1 | 5.44 | 424 | 80 | 6 | 29.0 | 4.77 | 1.03 | 4.37 | 2.18 | 1.38 | 20.57 |
| | | 5.44 | 424 | 80 | 12 | 31.03 | 5.30 | 0.88 | 3.95 | 2.05 | 1.32 | 22.51 |
| | | 5.44 | 424 | 80 | 23 | 24.14 | 4.05 | 1.34 | 5.43 | 2.68 | 1.73 | 20.87 |
| | | 5.44 | 424 | 80 | 36 | 28.16 | 5.20 | 1.17 | 4.52 | 2.36 | 1.56 | 19.98 |
| | | 5.44 | 424 | 80 | 43 | 25.05 | 3.97 | 1.05 | 4.22 | 2.01 | 1.29 | 19.84 |
| 2 | A-1 | 5.44 | 430 | 76 | 85 | 28.42 | 3.61 | 0.61 | 1.52 | 1.21 | 0.76 | 19.18 |
| 3 | A-1 | 5.44 | 432 | 90 | 43 | 28.89 | 4.93 | 1.29 | 3.08 | 2.83 | 1.80 | 16.77 |
| 4 | A-1 | 5.44 | 378 | 90 | 28 | 29.18 | 3.95 | 0.99 | 2.21 | 1.76 | 1.25 | 14.39 |
| 5 | A-1 | 1 | 317 | 90 | 13 | 27.74 | 4.40 | 1.03 | 3.36 | 2.11 | 1.66 | 11.14 |
| | | 1 | 345 | 90 | 30 | 17.39 | 2.20 | 1.31 | 2.43 | 3.06 | 1.98 | 6.84 |
| | | 1 | 364 | 90 | 75 | 20.34 | 2.33 | 1.31 | 3.62 | 3.07 | 2.01 | 7.18 |

| Ex. No. | Cat. | CONVERSION CONDITIONS | | | Sample Time (min.) | PRODUCT DISTRIBUTION - WT. % | | | | | | |
|---|---|---|---|---|---|---|---|---|---|---|---|---|
| | | Pressure (atm.) | TEMP. °C. | FLOW RATE CC./hr. | | $C_3H_6$ | $C_2H_6$ | $C_2H_4$ | $CH_4$ | CO | $CO_2$ | $H_2$ |
| 1 | A-1 | 5.44 | 424 | 80 | 6 | 13.60 | 1.44 | 13.92 | 4.85 | 1.43 | 1.12 | 0.34 |
| | | 5.44 | 424 | 80 | 12 | 10.85 | 1.64 | 12.06 | 5.01 | 1.68 | 1.38 | 0.36 |
| | | 5.44 | 424 | 80 | 23 | 15.72 | 1.29 | 15.64 | 4.54 | 1.21 | 0.96 | 0.40 |
| | | 5.44 | 424 | 80 | 36 | 14.22 | 1.56 | 13.25 | 4.55 | 1.68 | 1.40 | 0.39 |
| | | 5.44 | 424 | 80 | 43 | 15.98 | 1.67 | 15.45 | 5.26 | 2.10 | 1.48 | 0.63 |
| 2 | A-1 | 5.44 | 430 | 76 | 85 | 12.05 | 1.62 | 22.67 | 5.33 | 1.67 | 1.19 | 0.16 |
| 3 | A-1 | 5.44 | 432 | 90 | 43 | 17.93 | 0.69 | 13.50 | 2.79 | 4.88 | 0.61 | 0.02 |
| 4 | A-1 | 5.44 | 378 | 90 | 28 | 13.71 | 5.23 | 23.75 | 2.36 | 0.66 | 0.50 | 0.05 |
| 5 | A-1 | 1 | 317 | 90 | 13 | 15.18 | 3.52 | 27.76 | 1.46 | 0.00 | 0.63 | 0.00 |
| | | 1 | 345 | 90 | 30 | 35.36 | 0.21 | 27.16 | 1.58 | 0.04 | 0.38 | 0.05 |
| | | 1 | 364 | 90 | 75 | 34.42 | 0.58 | 23.21 | 1.39 | 0.01 | 0.44 | 0.07 |

EXAMPLE 6

Preparation of catalyst B-1

Ninety milliliters (48.2 g) of silicalite (S-115) from Union Carbide were heated for 48 hours under vacuum. The thus-treated silicalite was slowly added to 100 cc. of 0.45M $Th(NO_3)_4$ solution and mixed. After a period of time to ensure adequate impregnation of the silicalite, excess $Th(NO_3)_4$ solution was removed by filtering and the wet $Th(NO_3)_4$ impregnated silicalite was dried over a water bath and then heated to 180° C. in vacuum for 72 hours. The catalyst was cooled, packed in the reactor, and heated to 471° C. for 24 hours under a current of $N_2$ to convert $Th(NO_3)_4$ to $ThO_2$. $NO_2$ fumes were observed at the outlet of the reactor. The catalyst charged to the reactor weighed 40.1 g. and occupied a volume of 65 cc. This is catalyst B-1. The maximum possible $ThO_2$ would be 23% by weight.

The catalyst was cooled in $N_2$ to a temperature of 313° C. Methanol was fed to the reactor into contact with the catalyst. The parameters of the conversion are set forth in Table 3. The temperature profile of the reaction was as follows:

| Time (min.) | Temp. (°C.) |
|---|---|
| 0 | 313 |
| 3 | 343 |
| 7 | 377 |
| 8 | 440 |
| 13 | 445 |
| 16 (external heating stopped) | 452 |
| 23 | 453 |
| 30 | 450 |
| 37 | 447 |
| 70 (external heat started) | 425 |
| 80 (external heat stopped) | 431 |
| 86 | 442 |
| 100 | 438 |
| 108 | 432 |
| 118 | 425 |
| 122 | 421 |
| 130 | 415 |
| 132 | 414 |
| 136 | 410 |
| 140 | 408 |
| 143 | 405 |
| 172 | 383 |
| 187 | 368 |
| 197 | 357 |
| 200 | 332 |
| Methanol conversion | 100% |
| DME in product | 0 |
| % ($CH_2$) converted to organic liquid | 52.6 |
| WHSV = 1.27 hr.$^{-1}$ | |

The distribution of gaseous product is shown in Table 2.

EXAMPLE 7

A catalyst prepared as in Example 6 was used except that the initial temperature in the reactor was 342° C. A mixture of water and methanol in a 1 to 1 ratio by volume was fed into the reactor. The parameters of the conversion process and the distribution of the gaseous products are shown in Table 2. The temperature profile was as follows:

| Time (min.) | Temp. (°C.) |
|---|---|
| 0 | 342 |
| 4 | 363 |
| 5 | 367 |
| 10 | 375 |
| 11 (heating discontinued) | 386 |
| 12 | 391 |
| 14 | 391 |

-continued

| Time (min.) | Temp. (°C.) |
|---|---|
| 20 | 388 |
| 26 | 388 |
| 32 | 393 |
| % conversion of CH$_3$OH | 100 |
| % DME | 0 |
| % (CH$_2$) converted to organic liquid | 22.7 |
| WHSV = 1.27 hr.$^{-1}$ | |
| (based on total feed) | |
| WHSVM = 0.54 hr.$^{-1}$ | |
| (based on methanol feed only) | |

EXAMPLE 8

The same catalyst and methanol-water feed was used as in Example 7 except the initial temperature was 393° C. The conversion parameters and distributor of gaseous product are shown in Table 2. The temperature profile was as follows:

| Time (min.) | Temp. (°C.) |
|---|---|
| 0 | 393 |
| 4 | 416 |
| 9 | 421 |
| 28 | 417 |
| 32 | 423 |
| 33 | 423 |
| 35 | 426 |
| 41 | 429 |
| 42 | 429 |
| 45 | 434 |
| 46 | 433 |
| 53 | 432 |
| 56 | 432 |
| 69 | 433 |
| 73 | 433 |
| % Methanol conversion | 100 |
| % DME in product | 0 |
| % (CH$_2$) converted to organic liquid (aromatics) | 10.4 |
| WHSV = 2.4 hr.$^{-1}$ (based on total feed) | |
| WHSVM = 1.0 hr.$^{-1}$ (based on methanol feed) | |

The substantial increase in the production of C$_2$ and C$_3$ hydrocarbons, especially C$_2$H$_4$ and C$_3$H$_6$ and the decreased production of aromatics in Examples 7 and 8 are due to the addition of water to the feed.

EXAMPLE 9

A catalyst prepared as in Example 6 was maintained at a temperature of 329° C. in a flow of N$_2$; methanol was then fed to the reactor under the conditions indicated in Table 2. (The temperature rose to 458 and then remained steady; samples were collected at 454° C.) The distribution of the resultant gaseous product is shown in Table 2.

| Liquid products: | H$_2$O | 58.9 g. |
|---|---|---|
| | organic layer | 14.6 g. |
| % methanol conversion | | 100 |
| % (CH$_2$) converted to organic liquid | | 45 |
| DME in product | | 0 |
| WHSV | | 1.48 hr.$^{-1}$ |

EXAMPLE 10

A catalyst prepared as in Example 6 was maintained at a temperature of 378° C. in a current of N$_2$; air was passed through the catalyst for 1 hour and then the catalyst was cooled to 379° C. Methanol was fed to the reactor and heating was then discontinued. The parameters of the process and composition of the gaseous product are shown in Table 2.

| % CH$_3$OH conversion | 100 |
|---|---|
| DME in product | 0 |
| % (CH$_2$) converted to organic liquid | 42.1 |
| WHSV | 1.44 hr.$^{-1}$ |

EXAMPLE 11

Preparation of Catalyst B-2

Silicalite in an amount of 23.98 g. (50 cc.) and 18 cc. of a 0.45M solution of Th(NO$_3$)$_4$ were mixed to form a thick paste, which was dried to a powder (26.29 g.) by heating over a water bath and then in an oven at 160° C. at atmospheric pressure. The resultant catalyst contained 8.4% by weight ThO.

Conversion of Methanol

Fresh catalyst prepared as above was packed in the reactor and heated overnight in a current of N$_2$ at 343° C. Methanol was then fed to the reactor under a flow rate that was varied during the run.

The temperature, flow rate and distribution of the gaseous product are set forth in Table 2.

| Total CH$_3$OH fed: | 51.5 cc.; 40.74 g. |
|---|---|
| Total time of reaction: | 90 min. |
| Wt. of liquid product: | 9 g. |
| Organic layer | |
| H$_2$O | 22.72 g. |
| % CH$_2$ converted to organic liquid | 50.5 |
| WHSV | 0.63 hr.$^{-1}$ for 11 min. and then increased to 1.1 for remaining time |

EXAMPLE 12

Preparation of Catalyst B-3

Silicalite (60 g.) was mixed with thorium nitrate soln. (48 cc. diluted to 100 cc.) to form a slurry. This was mixed with slight excess of Na$_2$CO$_3$ soln. (110 cc. of 0.425M soln). Boiling Na$_2$CO$_3$ soln. was added to the boiling Th(NO$_3$)$_4$ all at once (copious frothing was observed) while stirring vigorously. After thorough mixing, the solution was filtered through Watman #1 filter paper with the aid of a vacuum. The composition was then washed with 500 ml. of deionized water and finally was dried over a water bath, to obtain 60.24 g. of catalyst. One half of this (30.12 g.) was slurried again with 10 cc. of K$_2$CO$_3$ soln. containing 0.0143 g. of K$_2$CO$_3$, dried again over a water bath, and calcined at 343° C. in a muffle furance, in a current of air (100 cc./min.) overnight; % ThO=8.9, % K$_2$CO$_3$≅0.05.

This catalyst, numbered B-3, was packed in the reactor.

Conversion of Methanol

The catalyst was heated to 354° C. in a current of N$_2$ (60 cc./min.) and then methanol was fed to the reactor the temperature rose to 391° C. and remained substantially constant for the length of the run. The other parameters of the conversion and composition of the gaseous product are set forth in Table 2.

| Time of run | 108 min. |
|---|---|
| % Conversion of (CH$_2$) to organic liquid | 42 |
| WHSV | 0.69 |

EXAMPLE 13

Catalyst B-3 was used.

A mixture of methanol and water (MeOH: H$_2$O, 9:1 by vol.) was fed to the reactor under the condition set forth in Table 2.

| WHSV = 0.74 hr.$^{-1}$ (based on total feed); | 0.65 (based on methanol feed) |
|---|---|
| % Conversion of CH$_3$OH | 100 |
| % DME in product | 0 |
| % (CH$_2$) converted to organic liquid | 47.2 |

The distribution of the gaseous product is set forth in Table 2.

EXAMPLE 14

Preparation of Catalyst B-4

Silicalite in an amount of 90 cc. (48 g.) was combined with 25 cc. of Th(NO$_3$)$_4$ solution which had been diluted to 100 cc. with water.

Phosphoric acid prepared by dissolving 28.5 g. P$_2$O$_5$ in 108 cc. of H$_2$O, and then diluting 15 cc. of this solution to 100 cc. was added to the silicalite-Th(NO$_3$)$_4$ slurry in small quantities with constant stirring until no precipitation was noticed in the supernatant solution. Then a slight excess of the acid was added (in all about 80 cc.). The solids in the beaker were separated by centrifuging, and washed three times using about 150 cc. of deionized water. The washings were also separated by centrifuging. Thorium phosphate content was estimated to be 6.6%.

The wet silicalite-thorium phosphate solid was dried over a boiling water bath and afterwards in vacuum at 140° C.

Sixty cc. (40 g.) of this catalyst numbered B-4 was packed in the reactor and calcined at 538° C.

Conversion of Methanol

After cooling the catalyst to 371° C. in a current of N$_2$, methanol was fed to the reactor under the conditions set forth in Table 2 for a period of 69 minutes; The distribution of gaseous products are also set forth in Table 2.

| % (CH$_2$) converted to organic liquid | 52 |
|---|---|
| % DME in product | 0 |
| WHSV | 0.6 hr.$^{-1}$ |

TABLE 2

| | | CONVERSION CONDITIONS | | | PRODUCT DISTRIBUTION - WT. % | | | | | | |
|---|---|---|---|---|---|---|---|---|---|---|---|
| Ex. No. | Cat. | Pressure (atm.) | TEMP. °C. | FLOW RATE CC./hr. | Sample Time (min.) | i-C$_4$H$_{10}$ | n-C$_4$H$_{10}$ | 1-C$_4$H$_8$ | i-C$_4$H$_8$ | trans 2-C$_4$H$_8$ | cis 2-C$_4$H$_8$ | C$_3$H$_8$ |
| 6 | B-1 | 1 | 400–445 | 53 | 76 | 39.0 | 7.7 | 1.26 | 10.28 | 2.34 | 3.75 | 15.67 |
| 7 | B-1 | 1 | 363–393 | 47 | 32 | 19.53 | 2.06 | 2.45 | 13.30 | 4.70 | 3.52 | 5.52 |
| 8 | B-1 | 1 | 393–433 | 89 | 73 | 15.78 | 1.99 | 2.66 | 13.2 | 3.25 | 4.8 | 5.84 |
| 9 | B-1 | 1 | 454 | 62 | 24 | 33.46 | 6.39 | 1.18 | 7.49 | 2.01 | 1.60 | 18.61 |
| 10 | B-1 | 1 | 468 | 60 | 58 | 32.65 | 4.93 | 0.89 | 5.54 | 1.55 | 1.03 | 20.04 |
| | | 1 | 468–446 | 60 | 98 | 34.68 | 4.56 | 0.84 | 6.11 | 1.46 | 1.02 | 18.87 |
| | | 1 | 446–436 | 60 | 106 | 35.15 | 5.08 | 0.91 | 6.71 | 1.75 | 1.15 | 18.29 |
| 11 | B-2 | 1 | 371 | 20 | 4 | 49.29 | 8.21 | 1.70 | 9.06 | 4.39 | 2.83 | 14.02 |
| | | 1 | 373 | 20 | 10 | 42.56 | 5.69 | 1.10 | 6.05 | 2.20 | 1.51 | 16.20 |
| | | 1 | 403 | 36 | 28 | 37.36 | 5.45 | 1.32 | 7.50 | 2.76 | 1.84 | 16.03 |
| | | 1 | 403 | 36 | 60 | 34.89 | 3.80 | 0.99 | 6.06 | 2.54 | 1.13 | 15.95 |
| | | 1 | 399 | 36 | 90 | 32.90 | 3.42 | 1.01 | 5.75 | 1.58 | 1.01 | 16.03 |
| 12 | B-3 | 1 | 388 | 26 | 32 | 36.46 | 3.49 | 1.48 | 7.55 | 2.56 | 1.75 | 11.13 |
| | | 1 | 391 | 26 | 47 | 34.04 | 2.91 | 1.40 | 7.16 | 2.25 | 1.54 | 11.15 |
| | | 1 | 391 | 26 | 65 | 33.81 | 3.68 | 1.84 | 9.08 | 3.69 | 2.50 | 10.14 |
| | | 1 | 391 | 26 | 163 | 31.48 | 2.66 | 1.43 | 7.42 | 2.43 | 1.57 | 10.20 |
| 13 | B-3 | 1 | 384 | 27 | 35 | 32.95 | 3.33 | 1.45 | 7.71 | 3.21 | 2.09 | 9.09 |
| | | 1 | 395 | 27 | 100 | 26.57 | 2.19 | 1.69 | 8.60 | 2.82 | 1.83 | 8.53 |
| | | 1 | 393 | 27 | 132 | 26.44 | 2.09 | 1.73 | 8.37 | 2.60 | 1.73 | 8.16 |
| | | 1 | 413 | 27 | 173 | 26.61 | 2.37 | 1.86 | 8.99 | 2.85 | 1.86 | 8.75 |
| 14 | B-4 | 1 | 377 | 30 | 13 | 47.13 | 8.74 | 0.26 | 1.79 | 1.02 | 0.51 | 25.11 |
| | | 1 | 393 | 30 | 18 | 42.90 | 5.35 | 0.41 | 2.31 | 0.68 | 0.54 | 27.11 |
| | | 1 | 412 | 30 | 46 | 37.42 | 6.19 | 0.53 | 2.92 | 1.06 | 0.66 | 29.96 |
| | | 1 | 414 | 30 | 65 | 37.33 | 6.56 | 0.52 | 3.10 | 1.03 | 0.65 | 29.74 |

| | | CONVERSION CONDITIONS | | | PRODUCT DISTRIBUTION - WT. % | | | | | | |
|---|---|---|---|---|---|---|---|---|---|---|---|
| Ex. No. | Cat. | Pressure (atm.) | TEMP. °C. | FLOW RATE CC./hr. | Sample Time (min.) | C$_3$H$_6$ | C$_2$H$_6$ | C$_2$H$_4$ | CH$_4$ | CO | CO$_2$ | H$_2$ |
| 6 | B-1 | 1 | 400–445 | 53 | 76 | 7.34 | 0.61 | 8.26 | 2.27 | 0.55 | 0.31 | 0.21 |
| 7 | B-1 | 1 | 363–393 | 47 | 32 | 28.55 | 0.44 | 13.99 | 2.08 | 1.14 | 2.6 | 0.12 |
| 8 | B-1 | 1 | 393–433 | 89 | 73 | 34.79 | 0.26 | 12.80 | 2.24 | 1.53 | 0.68 | 0.18 |
| 9 | B-1 | 1 | 454 | 62 | 24 | 11.43 | 1.05 | 7.43 | 6.64 | 1.50 | 0.74 | 0.47 |
| 10 | B-1 | 1 | 468 | 60 | 58 | 11.22 | 1.65 | 9.42 | 8.33 | 1.94 | 0.37 | 0.44 |
| | | 1 | 468–446 | 60 | 98 | 9.36 | 1.18 | 10.01 | 9.51 | 1.76 | 0.42 | 0.21 |
| | | 1 | 446–436 | 60 | 106 | 9.60 | 1.06 | 10.61 | 7.56 | 1.42 | 0.39 | 0.31 |
| 11 | B-2 | 1 | 371 | 20 | 4 | 2.12 | 0.38 | 4.18 | 1.90 | 0.00 | 1.22 | 0.68 |
| | | 1 | 373 | 20 | 10 | 11.34 | 0.74 | 7.77 | 2.36 | 0.00 | 1.86 | 0.63 |
| | | 1 | 403 | 36 | 28 | 14.62 | 0.63 | 8.23 | 3.38 | 0.00 | 0.62 | 0.24 |

TABLE 2-continued

| | | | | | | | | | | | |
|---|---|---|---|---|---|---|---|---|---|---|---|
| | | 1 | 403 | 36 | 60 | 14.80 | 0.83 | 11.91 | 4.95 | 1.34 | 0.55 | 0.27 |
| | | 1 | 399 | 36 | 90 | 15.31 | 1.39 | 14.01 | 5.58 | 1.51 | 0.34 | 0.17 |
| 12 | B-3 | 1 | 388 | 26 | 32 | 16.89 | 0.94 | 11.67 | 3.39 | 1.75 | 0.74 | 0.18 |
| | | 1 | 391 | 26 | 47 | 18.85 | 0.68 | 12.92 | 4.45 | 1.40 | 0.99 | 0.25 |
| | | 1 | 391 | 26 | 65 | 19.45 | 0.63 | 9.94 | 3.54 | 0.74 | 0.83 | 0.13 |
| | | 1 | 391 | 26 | 163 | 20.65 | 0.69 | 14.84 | 4.73 | 0.64 | 1.01 | 0.26 |
| 13 | B-3 | 1 | 384 | 27 | 35 | 18.80 | 0.69 | 10.20 | 1.74 | 4.10 | 3.41 | 1.22 |
| | | 1 | 395 | 27 | 100 | 26.11 | 0.53 | 15.43 | 3.46 | 1.06 | 1.00 | 0.19 |
| | | 1 | 393 | 27 | 132 | 25.96 | 0.54 | 16.23 | 3.54 | 1.08 | 1.25 | 0.28 |
| | | 1 | 413 | 27 | 173 | 25.26 | 0.61 | 14.27 | 4.00 | 1.21 | 1.12 | 0.25 |
| 14 | B-4 | 1 | 377 | 30 | 13 | 4.12 | 1.03 | 2.43 | 3.10 | 1.66 | 2.81 | 0.30 |
| | | 1 | 393 | 30 | 18 | 7.23 | 1.38 | 5.16 | 3.57 | 1.70 | 1.28 | 0.38 |
| | | 1 | 412 | 30 | 46 | 9.07 | 2.06 | 5.11 | 3.07 | 0.93 | 0.73 | 0.27 |
| | | 1 | 414 | 30 | 65 | 9.11 | 2.42 | 5.30 | 2.73 | 0.84 | 0.51 | 0.16 |

EXAMPLE 15

Preparation of Catalyst

The catalyst was prepared from silicalite in an amount of 25 g. (51 cc.) and 4 g. of $Zr(NO_3)_2$ in the following manner:

Zirconium nitrate was dissolved in 30 cc. of deionized water, and silicalite was added to form a slurry. After thorough mixing, the slurry was dried over a boiling water bath to dryness and then heated in the oven overnight at 140° C.; the catalyst contained about 8.0% ZrO.

This catalyst numbered C-1 was packed in the reactor and calcined overnight at 541° C. in a flow of air; $NO_2$ fumes were observed at the outlet of the reactor; 54 cc. of catalyst was packed in the reactor.

Conversion of Methanol

Methanol was fed to the reactor, which had been cooled to 379° C. in a current of $N_2$, under the conditions set forth in Table 3; the distribution of gaseous products is also set forth in Table 3.

| | |
|---|---|
| % conversion of Methanol | 100 |
| % DME in product | 0 |
| % ($CH_2$) conversion to organic liquid | 60 |
| WHSV | 0.92 hr.$^{-1}$ |

EXAMPLE 16

The catalyst used in Example 15 was regenerated in a current of air (60 cc./min.) at 515° C. and then cooled in a current of $N_2$ to 353° C.

A methanol-water mixture (1:1 by vol.) was fed to the reactor under the conditions set forth in Table 3 where the distribution of gaseous product has also been set forth.

| Weight of liquid product | |
|---|---|
| organic liquid | 16.46 g. |
| $H_2O$ | 32.17 g. |
| Theoretical yield of $H_2O$: | 34.4 g. |
| Theoretical yield of ($CH_2$): | 27.5 g. |
| % ($CH_2$) conversion to organic liquid | 26.9 |
| % conversion of methanol | 100 |
| % DME in gaseous product | 0 |
| WHSV | 2.36 (based on total feed) |
| WHSVM | 1.05 hr.$^{-1}$ (based on methanol) |

The increase in the proportion of $C_2$ and $C_3$ hydrocarbons especially $C_2H_4$ and $C_3H_6$ and the decrease in the proportion of aromatics in the product of Example 16, compared to the composition of the product of Example 15, are due largely to the presence of water in the feed.

TABLE 3

| | | CONVERSION CONDITIONS | | | | PRODUCT DISTRIBUTION - WT. % | | | | | | |
|---|---|---|---|---|---|---|---|---|---|---|---|---|
| Ex. No. | Cat. | Pressure (atm.) | TEMP. °C. | FLOW RATE CC./hr. | Sample Time (min.) | i-$C_4H_{10}$ | n-$C_4H_{10}$ | 1-$C_4H_8$ | i-$C_4H_8$ | trans 2-$C_4H_8$ | cis 2-$C_4H_8$ | $C_3H_8$ |
| 15 | C-1 | 1 | 462 | 31 | 4 | 23.47 | 6.16 | 2.12 | 9.63 | 439 | 2.97 | 14.91 |
| | | 1 | 416 | 31 | 13 | 29.48 | 6.24 | 1.54 | 6.87 | 2.80 | 1.96 | 18.95 |
| | | 1 | 419 | 31 | 45 | 29.90 | 4.48 | 1.15 | 5.20 | 1.59 | 1.01 | 20.98 |
| | | 1 | 400 | 31 | 72 | 33.83 | 4.43 | 1.00 | 5.13 | 1.28 | 0.86 | 21.52 |
| 16 | C-1 | 1 | 393 | 71 | 3 | 28.77 | 4.07 | 2.09 | 10.57 | 4.79 | 3.20 | 8.69 |
| | | 1 | 411 | 71 | 33 | 19.23 | 2.40 | 2.84 | 14.70 | 5.80 | 4.00 | 5.98 |
| | | 1 | 399 | 71 | 52 | 19.76 | 2.17 | 2.74 | 13.46 | 5.36 | 3.66 | 5.65 |
| | | 1 | 401 | 71 | 77 | 19.07 | 2.04 | 2.63 | 13.15 | 5.00 | 3.42 | 5.68 |

| | | CONVERSION CONDITIONS | | | | PRODUCT DISTRIBUTION - WT. % | | | | | | |
|---|---|---|---|---|---|---|---|---|---|---|---|---|
| Ex. No. | Cat. | Pressure (atm.) | TEMP. °C. | FLOW RATE CC./hr. | Sample Time (min.) | $C_3H_6$ | $C_2H_6$ | $C_2H_4$ | $CH_4$ | CO | $CO_2$ | $H_2$ |
| 15 | C-1 | 1 | 462 | 31 | 4 | 22.20 | 1.37 | 8.85 | 2.71 | 0.71 | 0.00 | 0.51 |
| | | 1 | 416 | 31 | 13 | 18.61 | 1.20 | 7.71 | 2.64 | 0.70 | 0.77 | 0.52 |
| | | 1 | 419 | 31 | 45 | 19.81 | 1.08 | 9.60 | 3.34 | 0.79 | 0.57 | 0.50 |
| | | 1 | 400 | 31 | 72 | 16.58 | 1.30 | 9.27 | 3.30 | 0.71 | 0.34 | 0.45 |
| 16 | C-1 | 1 | 393 | 71 | 3 | 23.05 | 0.20 | 10.26 | 0.70 | 0.00 | 3.48 | 0.12 |
| | | 1 | 411 | 71 | 33 | 31.24 | 0.21 | 11.99 | 1.07 | 0.26 | 0.20 | 0.09 |
| | | 1 | 399 | 71 | 52 | 31.17 | 0.21 | 14.24 | 1.08 | 0.33 | 0.10 | 0.07 |

TABLE 3-continued

| 1 | 401 | 71 | 77 | 32.94 | 0.21 | 14.14 | 1.20 | 0.33 | 0.10 | 0.08 |

EXAMPLE 17

Preparation of Catalyst D-1

A few ml. of TiCl₄ were poured directly into 75 cc. of water, whereby TiCl₄ hydrolyzed forming a white precipitate, probably of titanium oxychloride. On standing the precipitate dissolved. The clear solution was then treated with excess NH₄OH. A thick white precipitate of the hydroxide which formed was filtered and washed repeatedly with deionized water until free of Cl, and was then dissolved in minimum amount of 1:4 dilute HNO₃.

Thirty cc. of the resultant titanium nitrate solution was diluted with 30 cc. of deionized water and 32 g. (60 cc.) of silicalite was added; this mixture was heated to dryness over a water bath and then to 160° C. for 4 hours. NO₂ fumes were observed during heating.

A silicalite-TiO₂ catalyst containing 7% by weight of TiO₂ was obtained, which was packed in a reactor and calcined at 531° C. in air overnight and then cooled in a current of N₂ to 364° C. This catalyst is numbered D-1.

Conversion of Methanol

Methanol was fed to the reactor under the conditions indicated in Table 4 for 111 minutes. The distribution of the gaseous product is also shown in Table 4.

| % CH₃OH conversion | 100 |
| % DME | 0 |
| % (CH₂) conversion to organic liquid | 48.7 |
| WHSV | 0.64 hr.⁻¹ for first 75 min. |
| WHSV | 1.27 hr.⁻¹ 75 min. to 111 min. |

EXAMPLE 18

Catalyst D-1 from Example 17 was regenerated by calcination in air at 535° C. for 6 hours and then cooled to 364° C. in a current of N₂.

A mixture of methanol and water (1:1 by volume) was fed to the reactor for 50 minutes under the conditions indicated in Table 4. The total volume of methanol-water mixture fed the reactor was 122 cc. which contained 48.3 g. of methanol. The reaction was carried out for 50 min. and 80.25 g. of liquid product was collected containing 78 g. of H₂O and 2.25 of organic liquid.

% (CH₂) converted to organic liquid 10.7.

The distribution of the gaseous product is shown in Table 4.

| WHSV | 3.4 hr.⁻¹ (total feed) |
| WHSVM | 1.41 hr.⁻¹ (based on methanol feed) |

The reduced proportion of aromatics and the increase in the proportion of C₂H₄ and C₃H₆ in the product of Example 18 compared to that of Example 17 are largely the result of the addition of water to the feed of Example 18.

TABLE 4

| | | CONVERSION CONDITIONS | | | | PRODUCT DISTRIBUTION - WT. % | | | | | | |
|---|---|---|---|---|---|---|---|---|---|---|---|---|
| Ex. No. | Cat. | Pressure (atm.) | TEMP. °C. | FLOW RATE CC./hr. | Sample Time (min.) | i-C₄H₁₀ | n-C₄H₁₀ | 1-C₄H₈ | i-C₄H₈ | trans 2-C₄H₈ | cis 2-C₄H₈ | C₃H₈ |
| 17 | D-1 | 1 | 389 | 28 | 11 | 43.79 | 8.41 | 0.50 | 2.32 | 1.16 | 0.66 | 20.45 |
| | | 1 | 412 | 28 | 31 | 40.02 | 6.81 | 0.80 | 4.02 | 1.61 | 1.07 | 22.87 |
| | | 1 | 419 | 28 | 72 | 39.41 | 6.34 | 0.80 | 4.52 | 1.60 | 1.06 | 23.31 |
| | | 1 | 478 | 80 | 87 | 41.17 | 8.13 | 1.16 | 7.07 | 2.57 | 1.67 | 18.09 |
| | | 1 | 449 | 80 | 108 | 35.44 | 8.39 | 1.44 | 8.49 | 3.26 | 2.09 | 18.47 |
| 18 | D-1 | 1 | 460 | 146 | 7 | 24.77 | 4.13 | 2.57 | 12.34 | 5.40 | 3.73 | 9.60 |
| | | 1 | 449 | 146 | 22 | 18.29 | 2.84 | 2.60 | 12.46 | 5.07 | 3.42 | 8.28 |
| | | 1 | 443 | 146 | 45 | 13.03 | 1.39 | 2.95 | 11.65 | 5.22 | 3.61 | 4.10 |
| | | 1 | 424 | 146 | 50 | 24.14 | 2.62 | 2.66 | 12.92 | 4.81 | 3.17 | 8.66 |

| | | CONVERSION CONDITIONS | | | | PRODUCT DISTRIBUTION - WT. % | | | | | | |
|---|---|---|---|---|---|---|---|---|---|---|---|---|
| Ex. No. | Cat. | Pressure (atm.) | TEMP. °C. | FLOW RATE CC./hr. | Sample Time (min.) | C₃H₆ | C₂H₆ | C₂H₄ | CH₄ | CO | CO₂ | H₂ |
| 17 | D-1 | 1 | 389 | 28 | 11 | 5.84 | 1.69 | 3.81 | 2.42 | 6.88 | 0.52 | 1.55 |
| | | 1 | 412 | 28 | 31 | 10.97 | 1.01 | 5.17 | 3.56 | 0.87 | 0.84 | 0.36 |
| | | 1 | 419 | 28 | 72 | 11.08 | 1.50 | 5.72 | 3.76 | 0.60 | 0.00 | 0.29 |
| | | 1 | 478 | 80 | 87 | 9.26 | 1.45 | 4.89 | 3.64 | 0.45 | 0.20 | 0.25 |
| | | 1 | 449 | 80 | 108 | 9.70 | 1.26 | 5.94 | 4.59 | 0.46 | 0.31 | 0.18 |
| 18 | D-1 | 1 | 460 | 146 | 7 | 23.91 | 0.41 | 9.90 | 2.17 | 0.58 | 0.40 | 0.10 |
| | | 1 | 449 | 146 | 22 | 28.65 | 0.59 | 13.69 | 2.78 | 0.75 | 0.43 | 0.15 |
| | | 1 | 443 | 146 | 45 | 42.48 | 0.43 | 12.85 | 1.68 | 0.33 | 0.21 | 0.06 |
| | | 1 | 424 | 146 | 50 | 34.38 | 0.47 | 2.41 | 2.50 | 0.82 | 0.30 | 0.14 |

What we desire to claim and protect by Letters Patent is:

1. A process for converting methanol, dimethyl ether or a mixture thereof to a hydrocarbon product rich in iso-C₄ compounds comprising contacting methanol, dimethyl ether or a mixture thereof with a catalyst consisting essentially of silicalite impregnated with an oxide selected from the group consisting of thorium oxide, zirconium oxide, titanium oxide, and a combination thereof, at a temperature of about 300° C. to 550° C., whereby the gaseous product contains about 20% to 50% by weight of iso-$C_4$ compounds.

2. The process according to claim 1 in which methanol is contacted with said catalyst.

3. The process according to claim 1 in which said methanol, dimethyl ether or mixture thereof is combined with water.

4. The process according to claim 1 in which methanol, dimethyl ether or mixture thereof combined with up to 80% by weight of water is contacted with said catalyst.

5. The process according to claim 1 in which a mixture containing methanol in an amount of about 60 to 30% by weight and water in an amount of about 40 to 70% by weight is contacted with said catalyst.

6. The process according to claim 1 in which an equilibrium mixture of methanol, dimethyl ether and water is contacted with said catalyst.

7. The process according to claim 1 in which $C_2$, $C_3$ and aromatic hydrocarbons are produced during the conversion of methanol, dimethyl ether or a mixture thereof to said hydrocarbon product and in which water is added to said feed to increase the production of $C_2$ and $C_3$ hydrocarbons, to increase the olefinic content of the $C_2$ and $C_3$ hydrocarbons and to decrease the production of said aromatic hydrocarbons.

8. The process according to claim 1 in which said conversion is carried out at a temperature of about 330° to 455° C.

9. The process according to claim 1, in which said oxide is thorium oxide.

10. The process according to claim 1, in which said oxide is zirconium oxide.

11. The process according to claim 1, in which said oxide is titanium oxide.

12. The process according to claim 1, in which said crystalline solid has been impregnated with a mixture of said oxides.

13. The process according to claim 1, wherein said catalyst contains 0.5 to 30% by weight of said oxide.

14. The process according to claim 1, in which said catalyst contains about 2 to 15 parts by weight of said oxide.

15. The process according to claim 1 in which the gaseous product contains at least about 30% by weight of the iso-$C_4$ compounds.

16. A catalyst useful for converting methanol, dimethyl ether and a mixture thereof to a hydrocarbon product rich in iso-$C_4$ compounds consisting essentially of silicalite and from about 0.5 to 30% of oxide selected from the group consisting of thorium oxide, zirconium oxide, titanium oxide or a combination thereof impregnated therein.

17. The catalyst according to claim 16 which contains about 2 to 15 parts by weight of said oxide.

18. The catalyst according to claim 16 in which said oxide is thorium oxide.

19. The catalyst according to claim 16 in which said oxide is zirconium oxide.

20. The catalyst according to claim 16 in which said oxide is titanium oxide.

21. The catalyst according to claim 18 in which a combination of said oxides is impregnated in said silicalite.

* * * * *